United States Patent
Bailey et al.

(10) Patent No.: US 10,080,865 B2
(45) Date of Patent: Sep. 25, 2018

(54) MULTI-LUMEN CATHETERS FOR SMALL BODY VESSEL APPLICATIONS

(71) Applicant: Cook Medical Technologies LLC, Bloomington, IN (US)

(72) Inventors: Alyssa M. Bailey, Bloomington, IN (US); Brett O. Baker, Ellettsville, IN (US); Scott E. Boatman, Bloomington, IN (US); David A. Drewes, Jr., Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/595,773

(22) Filed: Jan. 13, 2015

(65) Prior Publication Data
US 2015/0196731 A1 Jul. 16, 2015

Related U.S. Application Data

(60) Provisional application No. 61/927,008, filed on Jan. 14, 2014.

(51) Int. Cl.
*A61M 25/00* (2006.01)
*A61L 29/04* (2006.01)
(Continued)

(52) U.S. Cl.
CPC ....... *A61M 25/0045* (2013.01); *A61L 29/049* (2013.01); *A61L 29/143* (2013.01); *A61M 25/005* (2013.01); *A61M 25/0026* (2013.01); *A61M 25/0053* (2013.01); *A61M 25/0054* (2013.01); *A61M 25/0032* (2013.01);
(Continued)

(58) Field of Classification Search
CPC .......... A61M 25/0021; A61M 25/0023; A61M 25/0026–25/003; A61M 25/0032; A61M 25/0043; A61M 25/0045; A61M 25/005; A61M 25/0052; A61M 25/0053;
(Continued)

(56) References Cited

U.S. PATENT DOCUMENTS

| 4,753,765 A | 6/1988 | Pande |
| 5,063,018 A | 11/1991 | Fontirroche et al. |

(Continued)

FOREIGN PATENT DOCUMENTS

| EP | 0420486 | 4/1991 |
| WO | WO1994001160 | 1/1994 |

(Continued)

OTHER PUBLICATIONS

European Patent Office, "Extended European Search Report," for application No. 15151173.0, dated Jun. 19, 2015, pp. 1-8.

*Primary Examiner* — Andrew Gilbert
*Assistant Examiner* — James D Ponton
(74) *Attorney, Agent, or Firm* — Buchanan Van Tuinen LLC (57) ABSTRACT

Catheters adapted for use in small body vessels are described. A catheter includes an elongate shaft having a main body that defines first and second lumens. An inner tubular member is disposed in the second lumen and is formed of a material that has a stiffness that is greater than a stiffness of the material forming the main body and that has an elastic modulus greater than or equal to about 400 MPa.

21 Claims, 3 Drawing Sheets

(51) Int. Cl.
*A61L 29/14* (2006.01)
*A61M 25/10* (2013.01)

(52) U.S. Cl.
CPC ....... *A61M 25/10* (2013.01); *A61M 2025/004* (2013.01); *A61M 2025/0037* (2013.01); *A61M 2025/0042* (2013.01); *A61M 2025/0063* (2013.01); *A61M 2025/1061* (2013.01)

(58) Field of Classification Search
CPC ...... A61M 25/0054; A61 2025/0036; A61M 2025/0037; A61M 2025/0063
See application file for complete search history.

(56) References Cited

U.S. PATENT DOCUMENTS

| | | | |
|---|---|---|---|
| 5,125,913 A | 6/1992 | Quackenbush | |
| 5,277,199 A | 1/1994 | DuBois et al. | |
| 5,374,245 A * | 12/1994 | Mahurkar | A61M 25/001 604/43 |
| 5,429,597 A * | 7/1995 | DeMello | A61M 25/005 604/103.09 |
| 5,464,394 A * | 11/1995 | Miller | A61M 25/005 604/103.1 |
| 5,538,510 A | 7/1996 | Fontirroche et al. | |
| 5,545,134 A * | 8/1996 | Hilaire | A61M 25/104 604/103.04 |
| 5,658,264 A | 8/1997 | Samson | |
| 5,685,841 A * | 11/1997 | Mackool | A61F 9/00745 604/22 |
| 5,702,373 A | 12/1997 | Samson | |
| 5,718,861 A | 2/1998 | Andrews et al. | |
| 5,824,173 A | 10/1998 | Fontirroche et al. | |
| 5,868,706 A | 2/1999 | Cox | |
| 6,004,310 A | 12/1999 | Bardsley et al. | |
| 6,273,876 B1 | 8/2001 | Klima et al. | |
| 6,368,302 B1 | 4/2002 | Fitzmaurice et al. | |
| 6,589,207 B1 | 7/2003 | Ei-Nounou | |
| 9,192,710 B2 | 11/2015 | Feng et al. | |
| 2001/0005552 A1 | 6/2001 | Berg et al. | |
| 2001/0011180 A1 | 8/2001 | Fitzmaurice et al. | |
| 2003/0050598 A1* | 3/2003 | Hayzelden | A61M 25/0136 604/95.04 |
| 2003/0105427 A1* | 6/2003 | Lee | A61M 25/1036 604/103.04 |
| 2003/0135198 A1 | 7/2003 | Berhow et al. | |
| 2004/0153049 A1 | 8/2004 | Hewitt et al. | |
| 2005/0043712 A1 | 2/2005 | Devens | |
| 2005/0267408 A1 | 12/2005 | Grandt et al. | |
| 2007/0005003 A1 | 1/2007 | Patterson et al. | |
| 2007/0016165 A1 | 1/2007 | Von Oepen et al. | |
| 2007/0213669 A1* | 9/2007 | Eskuri | A61M 25/0054 604/164.01 |
| 2007/0250149 A1 | 10/2007 | Von Oepen et al. | |
| 2007/0288053 A1 | 12/2007 | Trotta | |
| 2009/0024110 A1* | 1/2009 | Heideman | A61M 25/0012 604/528 |
| 2009/0163891 A1 | 6/2009 | Ewing et al. | |
| 2009/0171348 A1* | 7/2009 | Guo | A61M 25/0052 606/41 |
| 2010/0130925 A1* | 5/2010 | Haslinger | A61L 29/041 604/96.01 |
| 2010/0168717 A1 | 7/2010 | Grasse et al. | |
| 2011/0060276 A1 | 3/2011 | Schaeffer et al. | |
| 2011/0230718 A1 | 9/2011 | Akui | |
| 2013/0018307 A1 | 1/2013 | Lee et al. | |
| 2014/0046138 A1* | 2/2014 | Merk | A61M 25/0012 600/206 |

FOREIGN PATENT DOCUMENTS

| | | |
|---|---|---|
| WO | WO9965557 | 12/1999 |
| WO | WO03047679 | 6/2003 |
| WO | WO2012037507 | 3/2012 |

* cited by examiner

MULTI-LUMEN CATHETERS FOR SMALL BODY VESSEL APPLICATIONS

FIELD

The disclosure relates to medical devices. More particularly, the disclosure relates to multi-lumen catheters useful in intraluminal treatment procedures on animals, such as human beings.

BACKGROUND

In the pursuit of catheters that perform well in relatively small body vessels, such as vessels located below the knee in human beings, mere variation of some of the standard design choices considered during catheter development, such as wall thickness and lumen size, has required sacrifice of some aspects of catheter performance, such as pushability. As a result, a need remains for new catheters that are adapted to perform in small body vessels.

DESCRIPTION OF EMBODIMENTS

The following detailed description and the appended drawings describe and illustrate various example embodiments of multi-lumen catheters adapted for small body vessel applications. The description and illustration of these examples are provided to enable one skilled in the art to make and use a catheter. They are not intended to limit the scope of the claims in any manner.

As used herein, the term "small body vessel," and grammatically related terms, refers to any body vessel or portion of a body vessel that has a cross-sectional diameter less than about 5 mm.

As used herein, the term "elastic modulus," and grammatically related terms, refers to Modulus of Elasticity, or Young's Modulus.

Figure 1:
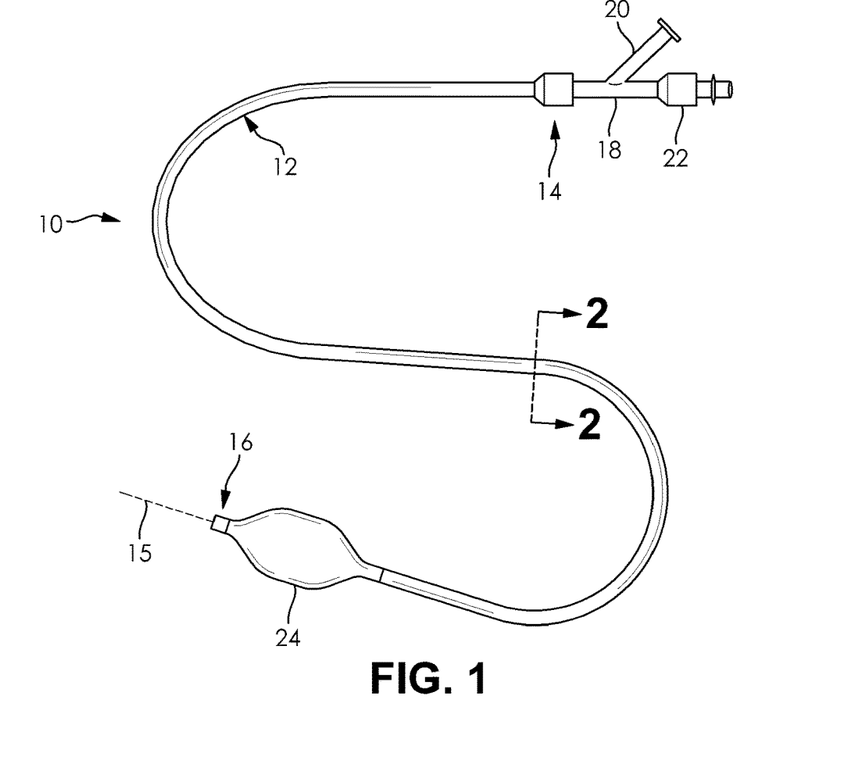
FIG. 1 is a perspective view of an example catheter.
Figure 2:
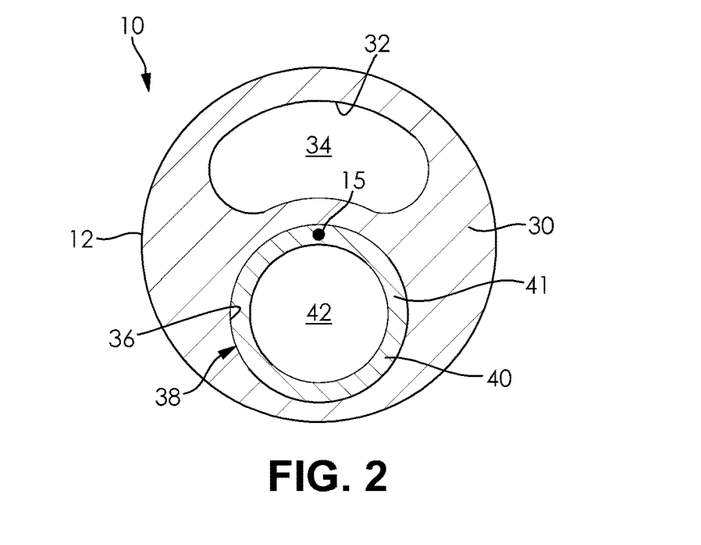
FIG. 2 is an enlarged cross-sectional view of the catheter illustrated in FIG. 1, taken along line 2-2.

FIGS. 1 and 2 illustrate an example catheter 10. The catheter 10 includes an elongate shaft 12 extending between a proximal end 14 and a distal end 16 and having a longitudinal axis 15. A hub 18 is disposed on the proximal end 14 and includes sidearm 20 and connector 22. A balloon 24 is attached to a distal portion of the elongate shaft 12 adjacent the distal end 16. The balloon 24 defines an interior chamber and has uninflated and inflated configurations. FIG. 1 illustrates the balloon 24 in the inflated configuration.

As best illustrated in FIG. 2, the elongate shaft 12 comprises a main body 30. The main body 30 has a first inner wall 32 that defines a first lumen 34 and a second inner wall 36 that defines a second lumen 38. An inner tubular member 40 is disposed within the second lumen 38. The inner tubular member 40 has a wall 41 that defines an inner lumen 42. In the illustrated embodiment, wall 41 is a circumferential wall.

The main body 30 extends along the entire length of the elongate shaft 12, from the proximal end 14 to the distal end 16. The main body 30 is a solid member that defines the first 34 and second 38 lumens such that each of the lumens 34, 38 extends along an axial length of the elongate shaft 12. Each of the lumens can extend along any suitable axial length of the elongate shaft and a skilled artisan will be able to select suitable axial lengths for each of the lumens in a catheter according to a particular embodiment based on various considerations, including the intended use of each of the lumens. In the illustrated embodiment, the first lumen 34 is an inflation lumen that is in communication with the interior chamber of the balloon 24. Passage of fluid through the inflation lumen inflates and deflates the balloon, moving it between its inflated and deflated configurations. As such, the first lumen 34 extends substantially along the entire length of the elongate shaft 12, from the proximal end 14 to a point on the longitudinal axis of the elongate shaft 12 that lies within the interior chamber of the balloon 24. Thus, in the illustrated embodiment, the first lumen 34 does not extend along the entire length of the elongate shaft 12. The second lumen 38 receives the inner tubular member 40, which defines the inner lumen 42. In the illustrated embodiment, the inner lumen 42 is a wireguide lumen, which allows the catheter 10 to be placed over a wireguide that has be previously placed in a body vessel, facilitating catheter navigation through the body vessel. For the illustrated embodiment, the second lumen 38 and, in turn, the inner lumen 42, extends along the entire length of the elongate shaft 12. As noted above, though, a catheter according to a particular embodiment can have a second lumen that extends along only a portion of the axial length of the elongate shaft. Thus, a wireguide lumen that extends along only a portion of the elongate shaft can be included in a catheter according to a particular embodiment, adapting that catheter for rapid exchange or short wire uses.

Each of the lumens can have any suitable shape and configuration and a skilled artisan will be able to select a suitable shape and configuration for each lumen in a catheter according to a particular embodiment based on various considerations, including the intended use of each of the lumens. In the illustrated embodiment, as best illustrated in FIG. 2, the first lumen 32 has a kidney cross-sectional shape while each of the second 38 and inner 42 lumens has a circular cross-sectional shape.

The lumens can be arranged within the main body of the elongate shaft in any suitable manner and a skilled artisan will be able to select a suitable arrangement for the lumens in a catheter according to a particular embodiment based on various considerations, including the relative sizes of the lumens and any desired flexibility of the elongate shaft. In the illustrated embodiment, the first lumen 34 is positioned above the central longitudinal axis 15 of the elongate shaft 12. Also, the second lumen 34 is positioned such that wall 41 of the inner tubular member 40 intersects the central longitudinal axis 15 of the elongate shaft 12.

Each of the main body 30 and the inner tubular member 40 can be formed of any suitable material, including known materials used in the manufacture of conventional catheters. The inventors have determined, though, that use of heat formable polyamide material, such as nylon and other materials used in the medical device arts, is advantageous.

Furthermore, a catheter in which the inner tubular member is formed of a relatively hard nylon material, as compared to the material forming the main body, provides desirable characteristics. The inventors have determined that catheters in which the inner tubular member 40 has an elastic modulus above a threshold value have particular advantages, including desirable column strength, stiffness and pushability even at relatively small sizes, including catheters in which the elongate shaft has a French Gauge of 4 or less than 4, making the catheters particularly well-suited for use in small body vessels. Furthermore, use of an inner tubular member 40 with an elastic modulus above a threshold value provides desirable low frictional characteristics for the inner lumen 42 defined by the inner tubular member 40.

The inventors have determined that use of an inner tubular member with an elastic modulus equal to or greater than about 400 MPa provides a catheter with desirable characteristics, including desirable pushability of the catheter. An inner tubular member with an elastic modulus equal to or greater than 400 MPa is considered advantageous. An inner tubular member with an elastic modulus greater than or equal to 400 MPa and less than or equal to about 4.2 GPa is also considered advantageous. An inner tubular member with an elastic modulus between about 400 MPa and about 4.2 GPa is also considered advantageous. An inner tubular member with an elastic modulus equal to or greater than 500 MPa is considered advantageous. An inner tubular member with an elastic modulus greater than or equal to 4.2 MPa and less than or equal to about 4 GPa is also considered advantageous. An inner tubular member with an elastic modulus between about 500 MPa and about 4 GPa is also considered advantageous. An inner tubular member with an elastic modulus equal to or greater than 400 MPa is considered advantageous. An inner tubular member with an elastic modulus greater than or equal to 800 MPa and less than or equal to about 3 GPa is also considered advantageous. An inner tubular member with an elastic modulus between about 800 MPa and about 3 GPa is also considered advantageous. Any suitable material can be used for the inner tubular member. For a catheter according to a particular embodiment, if it is desired to include an inner tubular member with an elastic modulus above a threshold level or within a critical range, as described above, any suitable material having the desired elastic modulus can be used. Non-limiting examples of suitable materials having a suitable elastic modulus in accordance with the parameters described above include polyether ether ketone (PEEK) and polyimide. Lubricious materials, such as polytetrafluoroethylene (PTFE) and high-density polyethylene (HDPE), can also be used for an inner tubular member.

The inventors have also determined that catheters in which the main body 30 is formed of a relatively flexible material, as compared to the material of the inner tubular member, have particular advantages, including desirable flexibility when being advanced through body vessels that include various curves, turns or other structural features.

Figure 3:
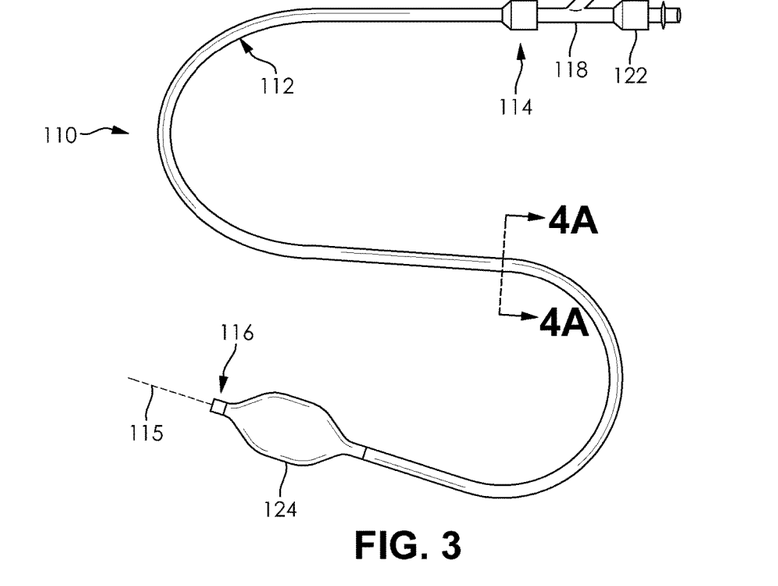
FIG. 3 is a perspective view of another example catheter.
Figure 4A:
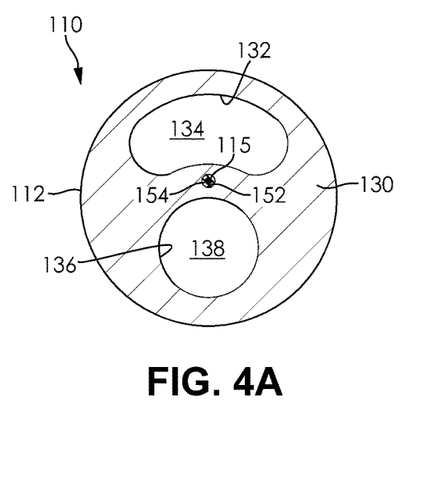
FIG. 4A is an enlarged cross-sectional view of the catheter illustrated in FIG. 3, taken along line 4A-4A.

FIGS. 3 and 4A illustrate another example catheter 110. The catheter 110 is similar to the catheter 10 illustrated in FIGS. 1 and 2 and described above, except as detailed below. Thus, the catheter 110 includes an elongate shaft 112 extending between a proximal end 114 and a distal end 116 and having a longitudinal axis 115. A hub 118 is disposed on the proximal end 114 and includes sidearm 120 and connector 122. A balloon 124 is attached to a distal portion of the elongate shaft 112 adjacent the distal end 116. The balloon 124 defines an interior chamber and has uninflated and inflated configurations. FIG. 3 illustrates the balloon 124 in the inflated configuration.

The elongate shaft 112 comprises a main body 130. In this embodiment, the main body 130 has a first inner wall 132 that defines a first lumen 134, a second inner wall 136 that defines a second lumen 138, and a third inner wall 150 that defines a third lumen 152. Each of the lumens 134, 138, 152 extends along an axial length of the elongate shaft 112. In contrast to the embodiment illustrated in FIGS. 1 and 2 and described above, the catheter 110 does not include an inner tubular member in any of the lumens 134, 138, 152. Rather, to provide the desired stiffness, a stiffening member 154 is disposed in the third lumen 152. The stiffening member 154 also extends along an axial length of the elongate shaft 112.

Any suitable member can be used for the stiffening member and a skilled artisan will be able to select an appropriate stiffening member for a catheter according to a particular embodiment based on various considerations, including the desired stiffness of the overall catheter. Non-limiting examples of suitable stiffening members include wires, rods, and braided strands. Furthermore, any suitable material can be used for the stiffening member. Non-limiting examples of suitable materials included metal and polymeric materials. Non-limiting examples of suitable metals include stainless steel, superelastic materials, such as shape memory alloys, including Nickel Titanium alloys, and other metal materials. Non-limiting examples of polymeric materials include nylon and other suitable polymeric materials. A stainless steel rod is considered suitable for use as a stiffening member.

The stiffening member can be positioned within the main body of the elongate shaft in any suitable location. A skilled artisan will be able to select an appropriate location in a catheter according to a particular embodiment based on various considerations, including the size and position of the lumens of the catheter. In the illustrated embodiment, the third inner wall 150 is positioned within the main body 130 such that the third lumen 152 extends along the longitudinal axis 115 of the elongate shaft 112. This positioning of the third lumen 152 ensures that the stiffening member 154 extends along the longitudinal axis 115 of the elongate shaft 112.

The stiffening member can extend along any suitable axial length of the elongate shaft and a skilled artisan will be able to select suitable axial lengths for the stiffening member in a catheter according to a particular embodiment based on various considerations, including the desired overall stiffness of the catheter and the presence or absence of any additional functional components. For example, the illustrated example embodiment includes a balloon 124. The stiffening member 152 extends from the proximal end 114 of the elongate shaft 112, through the portion containing the balloon 124 and into the distal end 116 of the elongate shaft 112. The stiffening member 154 does not extend to the very end of the elongate shaft 112, though, in order to provide a degree of flexibility on the distal tip of the elongate shaft 112, distal to the balloon 124. Alternative axial lengths can be used, however, including an axial length in which the stiffening member extends along the entire axial length of the elongate shaft 112 and lengths in which the stiffening member extends along only a portion of the axial length of the elongate shaft 112.

While the illustrated example catheter 110 includes a single stiffening member 154, it is noted that any suitable number of stiffening members can be used in a catheter according to a particular embodiment. A skilled artisan will be able to select an appropriate number of stiffening members for a particular catheter based on various considerations, including any desired overall stiffness and/or pushability of the catheter. For embodiments that include multiple stiffening members, the main body of the elongate shaft can include one or more additional lumens within which the additional stiffening members can be disposed.

Figure 4B:
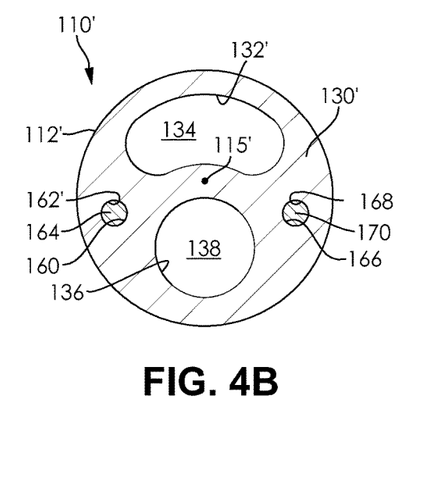
FIG. 4B is an enlarged cross-sectional view of an alternative example catheter.

FIG. 4B illustrates an alternative catheter 110' that includes two stiffening members 164, 170. The catheter 110' is similar to the catheter 110 illustrated in FIG. 4A and described above, except as detailed below. Thus, the catheter 110' includes an elongate shaft 112' extending between a proximal end and a distal end (not illustrated in FIG. 4B).

In this alternative embodiment, the main body 130' includes a third inner wall 160 that defines a third lumen 162, and a fourth inner wall 166 that defines a fourth lumen 168. A first stiffening member 164 is disposed in the third lumen 162 and a second stiffening member 170 is disposed in the fourth lumen 168.

In embodiments that include multiple stiffening members, any suitable arrangement of the stiffening members relative to each other and to the main body and other lumens of the catheter can be used. A skilled artisan will be able to select an appropriate arrangement of stiffening members for a particular catheter based on various considerations, including the size and position of the lumens of the catheter. In the illustrated embodiment, the third 162 and fourth 168 lumens are positioned on the same side of the longitudinal axis 115' of the elongate shaft 112 in the cross-sectional plane. Also, the third 162 and fourth 168 lumens, and, as a result, the first 164 and second 170 stiffening members, are positioned on a cross-sectional plane such that an obtuse angle is formed between a line segment connecting a longitudinal axis of the first 164 stiffening member and the longitudinal axis 115' of the elongate shaft 112 and a line segment connecting a longitudinal axis of the second 170 stiffening member and the longitudinal axis 115' of the elongate shaft 112.

Figure 5A:
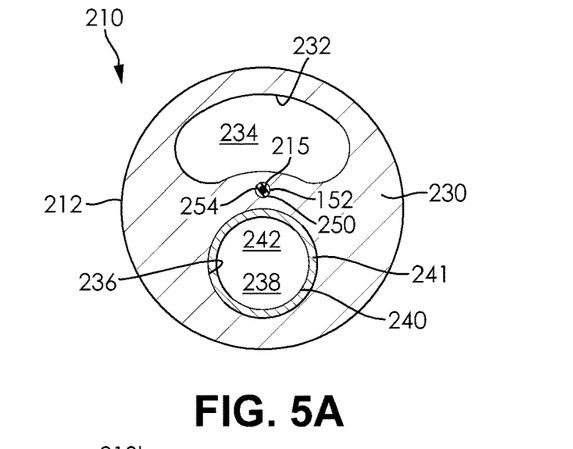
FIG. 5A is an enlarged cross-sectional view of another example catheter.

FIG. 5A illustrates a cross-section of another example catheter 210. The catheter 210 is similar to the catheter 10 illustrated in FIGS. 1 and 2 and described above, except as detailed below. Thus, the catheter 210 includes an elongate shaft 212 extending between a proximal end and a distal end (not illustrated in the Figures) and having a longitudinal axis 215. The elongate shaft 212 comprises a main body 230. The main body 230 has a first inner wall 232 that defines a first lumen 234 and a second inner wall 236 that defines a second lumen 238. An inner tubular member 240 is disposed within the second lumen 238. The inner tubular member 240 has a wall 241 that defines an inner lumen 242. In the illustrated embodiment, wall 241 is a circumferential wall.

In this embodiment, the main body 230 of the elongate shaft 212 defines a third inner wall 250 that defines a third lumen 252 in a similar manner as in the catheter 110 illustrated in FIGS. 3 and 4A. Each of the lumens 234, 238, 252 extends along an axial length of the elongate shaft 212.

In this embodiment, the catheter 210 includes both an inner tubular member 240 disposed within the second lumen 238 and a stiffening member 254 disposed in the third lumen 252. This structural arrangement is considered particularly well-suited for providing desirable overall stiffness to the catheter 210, particularly when the stiffening member 254 is positioned along the longitudinal axis 215 of the elongate shaft 212, as illustrated. Any suitable positioning of the stiffening member can be used, though.

As with the embodiment illustrated in FIGS. 1 and 2 and described above, the main body 230 and the inner tubular member 240 can be formed of any suitable material or materials, but catheters in which the inner tubular member 240 is formed of a relatively hard material as compared to the material forming the main body 230 provide desirable characteristics, particularly when a stiffening member is included in the catheter, such as in the illustrated embodiment.

Figure 5B:
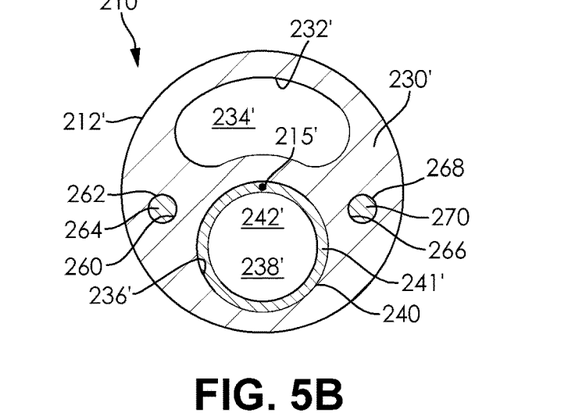
FIG. 5B is an enlarged cross-sectional view of an alternative example catheter.

FIG. 5B illustrates a cross-section of an alternative catheter 210'. The catheter 210' is similar to the catheter 210 illustrated in FIG. 5 and described above, except as detailed below. Thus, the catheter 210' includes an elongate shaft 212' extending between a proximal end and a distal end (not illustrated in the Figures) and having a longitudinal axis 215'. The elongate shaft 212' comprises a main body 230'. The main body 230' has a first inner wall 232' that defines a first lumen 234' and a second inner wall 236' that defines a second lumen 238'. An inner tubular member 240' is disposed within the second lumen 238'. The inner tubular member 240' has a wall 241' that defines an inner lumen 242'. In the illustrated embodiment, wall 241' is a circumferential wall.

In this embodiment, the main body 230' includes a third inner wall 260 that defines a third lumen 262, and a fourth inner wall 266 that defines a fourth lumen 268. A first stiffening member 264 is disposed in the third lumen 262 and a second stiffening member 270 is disposed in the fourth lumen 268.

In this embodiment, the catheter 210' includes both an inner tubular member 240' disposed within the second lumen 238' and first 264 and second 270 stiffening members disposed in the third 262 and fourth 268 lumens, respectively. This structural arrangement is considered particularly well-suited for providing desirable overall stiffness to the catheter 210', particularly when the stiffening members 264, 270 are positioned as illustrated. Any suitable positioning of the stiffening members can be used, though.

As with the embodiment illustrated in FIGS. 1 and 2 and described above, the main body 230' and the inner tubular member 240' can be formed of any suitable material or materials, but catheters in which the inner tubular member 240' is formed of a relatively hard material as compared to the material forming the main body 230' provide desirable characteristics, particularly when multiple stiffening members are included in the catheter, such as in the illustrated embodiment.

Figure 5C:
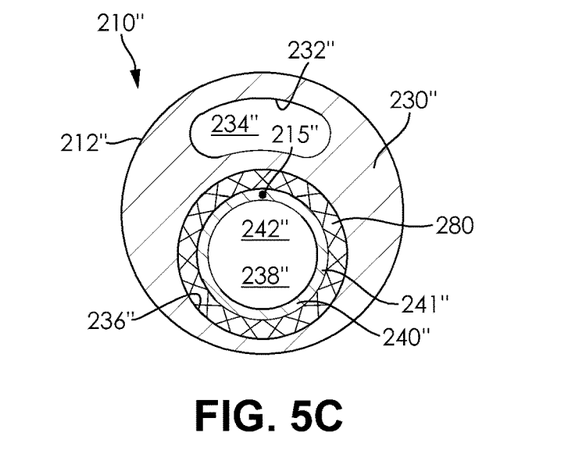
FIG. 5C is an enlarged cross-sectional view of another alternative example catheter.

FIG. 5C illustrates a cross-section of another alternative catheter 210". The catheter 210" is similar to the catheter 210 illustrated in FIG. 5 and described above, except as detailed below. Thus, the catheter 210" includes an elongate shaft 212" extending between a proximal end and a distal end (not illustrated in the Figures) and having a longitudinal axis 215". The elongate shaft 212" comprises a main body 230". The main body 230" has a first inner wall 232" that defines a first lumen 234" and a second inner wall 236" that defines a second lumen 238". An inner tubular member 240" is disposed within the second lumen 238". The inner tubular member 240" has a wall 241" that defines an inner lumen 242". In the illustrated embodiment, wall 241" is a circumferential wall.

In this embodiment, a reinforcement tubular member 280 is disposed over the inner tubular member 240" and within the second lumen 238". The inclusion of a reinformcement tubular member in this structural arrangement provides the desired overall stiffness for the catheter while elimating the need for additional lumens for containing stiffening members. It is noted, though, that one or more additional lumens and one or more stiffening members can be included in a catheter according to an embodiment that includes a reinforcement tubular member.

Any suitable tubular member can be used as a reinforcement tubular member and a skilled artisan will be able to select an appropriate tubular member for inclusion in a catheter according to a particular embodiment based on various considerations, including any desired overall stiffness of the catheter and the size of the clearance that exists between the inner tubular member and the inner wall of the main body that defines the lumen that receives the inner tubular member and the reinforcement tubular member. Examples of suitable tubular members include polymeric tubular members, braided tubular members, and coil tubular members. In the embodiment illustrated in FIG. 5C, the reinforcement tubular member 280 comprises a braided tubular member comprising metal fibers braided together to form the reinforcement tubular member. Braided tubular members are considered advantageous at least because they contribute to the axial strength of the catheter while also providing a desirable degree of flexibility to the overall catheter. Also, braided tubular members can be placed in catheters having a relatively small clearance between the inner tubular member and the inner wall of the main body that defines the lumen that receives the inner tubular member and the reinforcement tubular member.

If included in a catheter according to a particular embodiment, any suitable braided tubular member can be used and a skilled artisan will be able to select an appropriate braided tubular member based on various considerations, including any desired stiffness and flexibility of the catheter. When constructing such a catheter, a skilled artisan can vary various structural features of the braided tubular member to achieve desired stiffness and flexibility, such as the pitch angle of the wire members included in the braid, the number of wire members included in the braid, the diameter of the wire members included in the braid, the density of the wire members within the braid, the pattern of the braid, and the material used for the wire members included in the braid. Any suitable combination of these structural features can be used. It is noted that wire members having any suitable size, shape, configuration can be used in a braided tubular member and the term "wire member" does not require any particular size, shape or configuration. Furthermore, wire members made of any suitable material can be used in a braided tubular member. Examples of suitable materials include metallic materials, synthetic materials, natural materials, MRI compatible materials (i.e., non-magnetic), and radiopaque materials.

As with the embodiment illustrated in FIGS. 1 and 2 and described above, the main body 230" and the inner tubular member 240" can be formed of any suitable material or materials, but catheters in which the inner tubular member 240" is formed of a relatively hard material as compared to the material forming the main body 230" provide desirable characteristics, particularly when multiple stiffening members are included in the catheter, such as in the illustrated embodiment.

While the illustrated example catheters include an attached hub, such as hub 18 shown in FIG. 1, it is noted that the inclusion of accessory components, such as the illustrated hub 18, is considered optional. Indeed, an embodiment of a catheter can include only an elongate shaft fabricated as described herein. If inclusion of accessory components is desired, though, for a catheter according to a particular embodiment, any suitable catheter accessory component can be included, such as connectors, ports, valves, other types of hubs, and any other suitable catheter accessory component now known or later developed.

Furthermore, while the illustrated example catheters are balloon catheters adapted for inflation and deflation of an attached balloon, such as balloon 24 shown in FIG. 1, it is noted that the inclusion of a balloon or any other functional component or components is also considered optional. A balloon catheter is only one example of a type of catheter that can be fabricated as an embodiment; any type of catheter can be fabricated in accordance with the disclosure.

All components of the catheters can be made from any suitable material. Skilled artisans will be able to select appropriate materials for the components of a catheter according to a particular embodiment based on various considerations, including the nature of the body vessel within which the particular catheter is intended to be used. Examples of suitable materials include plastics and other materials used in the manufacture of conventional catheters, and newly-developed materials determined to be suitable for use in components of medical catheters. As described above, the inventors have determined that, in embodiments that include an inner tubular member, use of a relatively hard material for the inner tubular member and a relatively flexible material for the main body provides desirable characteristics. Furthermore, in these embodiments, use of a lubricious inner tubular member is considered advantageous at least because it facilitates smooth tracking of the catheter along a guidewire. Use of a relatively stiff and lubricious material, such as those described above, for an included inner tubular member facilitates tracking of the inventive catheters over guidewires that have come into contact with blood. In these embodiments, inclusion of these materials can avoid the catheter from "locking up" such a guidewire. This use of such relatively different materials is considered optional, though.

The catheters can be fabricated in any suitable manner and using any suitable technique. Skilled artisans will be able to select an appropriate technique for fabricating a catheter according to a particular embodiment based on various considerations, including the nature of the materials used for the various components.

For embodiments including an inner tubular member disposed within a lumen defined by a main body of an elongate shaft, the inner tubular member can be coextruded with the main body or can be formed before or after the main body is formed, such as by a separate extrusion process. For embodiments including one or more stiffening members, each of the stiffening members can be positioned during extrusion of the main body of the elongate shaft or inserted into the appropriate lumen after the main body is formed. For example, a first lumen can be extruded first and the one or more stiffening members can then be attached to the resulting tubular member. Then, another extrusion can be performed over the assembly of the tubular member and the one or more stiffening members. The second extrusion can form an additional lumen to provide a main body and stiffening member, such as those described herein. For embodiments including a braided member, the braided member can be positioned during extrusion of the main body of the elongate shaft or inserted into the appropriate lumen after the main body is formed. For example, a braided member can be placed around an inner tubular member and the main body can then be extruded over the resulting assembly or the resulting assembly can be inserted into the appropriate lumen after the main body is formed.

Catheters according to particular embodiments, including those described and illustrated herein, provide desirable column strength and pushability even at relatively small sizes, including catheters in which the elongate shaft has a French Gauge of 5 or less than 5, a French Gauge of 4 or less than 4, or a French Gauge of 3 or less than 3, making the catheters particularly well-suited for use in small body vessels. It is understood, though, that catheters of any size can be fabricated in accordance with the teachings of the disclosure.

Those with ordinary skill in the art will appreciate that various modifications and alternatives for the described and illustrated embodiments can be developed in light of the overall teachings of the disclosure. Accordingly, the particular structures and methods disclosed are intended to be illustrative only and not limiting as to the scope of the invention, which is to be given the full breadth of the claims and any and all equivalents thereof.

We claim:

1. A catheter, comprising:
    an elongate shaft having a proximal end, a distal end, a main body extending between the proximal end and the distal end, a distal portion disposed adjacent to the distal end of the elongate shaft, and a longitudinal axis, the main body formed of a first material and defining first, second, and third lumens, the third lumen disposed between the first lumen and the second lumen;
    a balloon disposed on the distal portion of the elongate shaft, the balloon defining an interior chamber in communication with the first lumen and having uninflated and inflated configurations;
    an inner tubular member disposed in the second lumen and extending along an axial length of the elongate shaft, the inner tubular member formed of a second material; and
    a stiffening member disposed within the third lumen, extending through the distal portion of the elongate shaft, and having a solid cross-section;
    wherein the first material has a first stiffness, the second material has a second stiffness, and the second stiffness is greater than the first stiffness; and
    wherein the second material has an elastic modulus greater than or equal to about 400 MPa.

2. The catheter of claim 1, wherein one of the first material and the second material comprises a polyamide material.

3. The catheter of claim 2, wherein one of the first material and the second material comprises a nylon material.

4. The catheter of claim 1, wherein both of the first material and the second material comprise a polyamide material.

5. The catheter of claim 1, wherein both of the first material and the second material comprise a nylon material.

6. The catheter of claim 1, wherein the inner tubular member comprises a wall and the wall intersects the longitudinal axis of the elongate shaft.

7. The catheter of claim 1, wherein the first lumen has a kidney cross-sectional shape.

8. The catheter of claim 1, wherein the elongate shaft has a French Gauge of 4 or less than 4.

9. The catheter of claim 1, wherein the stiffening member comprises a metal.

10. The catheter of claim 9, wherein the stiffening member comprises stainless steel.

11. The catheter of claim 1, wherein the stiffening member comprises a polymeric material.

12. The catheter of claim 1, wherein the main body defines a fourth lumen.

13. The catheter of claim 12, further comprising a second stiffening member disposed within the fourth lumen.

14. The catheter of claim 1, further comprising a reinforcement tubular member disposed over the inner tubular member and within the second lumen.

15. The catheter of claim 14, wherein the reinforcement tubular member comprises a braided member.

16. The catheter of claim 1, wherein the stiffening member is a rod.

17. The catheter of claim 1, wherein the stiffening member is a wire member.

18. The catheter of claim 1, wherein the third lumen has a central axis; and
    wherein a hypothetical plane extending orthogonally to a cross-section of the elongate shaft extends through the central axis of the third lumen and each of the first and second lumens.

19. The catheter of claim 18, wherein the stiffening member intersects the longitudinal axis of the elongate shaft.

20. A catheter, comprising:
    an elongate shaft having a proximal end, a distal end, a main body extending between the proximal end and the distal end, a distal portion disposed adjacent to the distal end of the elongate shaft, and a longitudinal axis, the main body formed of a first material and defining first, second and third lumens, the third lumen disposed between the first lumen and the second lumen;
    a balloon disposed on the distal portion of the elongate shaft, the balloon defining an interior chamber in communication with the first lumen and having uninflated and inflated configurations;
    an inner tubular member disposed in the second lumen and extending along an axial length of the elongate shaft, the inner tubular member formed of a second material; and
    a stiffening member disposed within the third lumen, extending through the distal portion of the elongate shaft, and having a solid cross-section;
    wherein the elongate shaft has a French Gauge of 5 or less than 5;
    wherein the first material has a first stiffness, the second material has a second stiffness, and the second stiffness is greater than the first stiffness; and
    wherein the second material has an elastic modulus greater than or equal to about 400 MPa.

21. A catheter, comprising:
    an elongate shaft having a proximal end, a distal end, a main body extending between the proximal end and the distal end, a distal portion disposed adjacent to the distal end of the elongate shaft, and a longitudinal axis, the main body formed of a first material and defining first, second, and third lumens, the third lumen disposed between the first lumen and the second lumen;
    a balloon disposed on the distal portion of the elongate shaft, the balloon defining an interior chamber in communication with the first lumen and having uninflated and inflated configurations;
    an inner tubular member disposed in the second lumen and extending along an axial length of the elongate shaft, the inner tubular member formed of a second material;
    a braided member disposed over the inner tubular member and within the second lumen; and
    a stiffening member disposed within the third lumen, extending through the distal portion of the elongate shaft, and having a solid cross-section;
    wherein the elongate shaft has a French Gauge of 5 or less than 5;

wherein the first material has a first stiffness, the second material has a second stiffness, and the second stiffness is greater than the first stiffness; and wherein the second material has an elastic modulus greater than or equal to about 400 MPa.

* * * * *